(12) United States Patent
Hayashi

(10) Patent No.: US 6,573,513 B2
(45) Date of Patent: Jun. 3, 2003

(54) FLUORESCENCE IMAGING APPARATUS

(75) Inventor: Katsumi Hayashi, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/760,769

(22) Filed: Jan. 17, 2001

(65) Prior Publication Data

US 2001/0009269 A1 Jul. 26, 2001

(30) Foreign Application Priority Data

Jan. 17, 2000 (JP) ........................................ 2000-007304

(51) Int. Cl.[7] .............................................. G01N 21/64
(52) U.S. Cl. .................................. 250/458.1; 250/459.1
(58) Field of Search ................................ 600/181, 160, 600/178; 358/483; 438/60; 257/222, 225; 250/458.1, 459.1, 461.1

(56) References Cited

U.S. PATENT DOCUMENTS

| | | | | |
|---|---|---|---|---|
| 4,821,117 A | * | 4/1989 | Sekiguchi | 358/98 |
| 5,590,660 A | * | 1/1997 | MacAuley et al. | 128/664 |
| 5,693,948 A | * | 12/1997 | Sayed et al. | 250/370 |
| 5,749,830 A | * | 5/1998 | Kaneko et al. | 600/160 |
| 5,827,190 A | * | 10/1998 | Palcic et al. | 600/476 |
| 5,900,949 A | * | 5/1999 | Sampas | 358/482 |
| 5,971,918 A | * | 10/1999 | Zanger | 600/160 |
| 6,140,147 A | * | 10/2000 | Murakami et al. | 438/79 |

* cited by examiner

Primary Examiner—Constantine Hannaher
Assistant Examiner—Timothy Moran
(74) Attorney, Agent, or Firm—Sughrue Mion, PLLC

(57) ABSTRACT

An excitation light irradiating device irradiates excitation light to a measuring site. A fluorescence imaging device performs an imaging operation for detecting a fluorescence image formed with fluorescence, which has been produced from the measuring site when the excitation light is irradiated to the measuring site. An illumination device irradiates illumination light to the measuring site. An ordinary imaging device performs an imaging operation for detecting an ordinary image formed with reflected light of the illumination light. A controller controls such that the imaging operation for detecting the fluorescence image and the imaging operation for detecting the ordinary image are performed alternately, and such that an operation for throwing off accumulated electric charges is performed before the imaging operation of the fluorescence imaging device is performed and/or before the imaging operation of the ordinary imaging device is performed.

13 Claims, 9 Drawing Sheets

| | |
|---|---|
| IMAGING OPERATION FOR DETECTING AN ORDINARY IMAGE |  |
| IMAGING OPERATION FOR DETECTING A FLUORESCENCE IMAGE |  |
| DISPLAY |    |
| | ORDINARY IMAGE  FLUORESCENCE IMAGE |

FLUORESCENCE IMAGING APPARATUS

BACKGROUND OF THE INVENTION

1. Field of the Invention

This invention relates to a fluorescence imaging apparatus for performing an imaging operation for detecting a fluorescence image formed with fluorescence, which has been produced from a measuring site when excitation light is irradiated to the measuring site, and an imaging operation for detecting an ordinary image formed with reflected light, which has been reflected by the measuring site when illumination light is irradiated to the measuring site.

2. Description of the Related Art

It has heretofore been known that, in cases where excitation light having wavelengths falling within an excitation wavelength range for an intrinsic dye in a living body is irradiated to the living body, a fluorescence spectrum of fluorescence produced by the intrinsic dye in the living body varies for normal tissues and diseased tissues. FIG. 9 shows typical fluorescence spectra of the fluorescence produced from normal tissues and the fluorescence produced from diseased tissues, which fluorescence spectra have been measured by the inventors. As illustrated in FIG. 9, the fluorescence produced from the normal tissues has a high light intensity as a whole and has a particularly high light intensity at a blue wavelength region. Also, the fluorescence produced from the diseased tissues has a low light intensity as a whole and has a flat spectral pattern. It is assumed that the thus produced fluorescence results from superposition of the fluorescence produced by various kinds of intrinsic dyes in the living body, such as FAD, collagen, fibronectin, and porphyrin.

There have heretofore been proposed systems wherein, by the utilization of the characteristics such that the fluorescence spectrum of the fluorescence produced by the intrinsic dye in the living body varies for the normal tissues and the diseased tissues, the fluorescence, which has been produced from a measuring site in a living body when the excitation light is irradiated to the measuring site, is imaged, the thus detected fluorescence image is displayed as a color image or a pseudo color image on a monitor, and location and an infiltration range of the diseased tissues are thereby displayed as a change in color. In such systems, fluorescence imaging apparatuses for imaging the fluorescence, which has been produced from the measuring site in the living body when the excitation light is irradiated to the measuring site, are utilized.

Ordinarily, the fluorescence imaging apparatuses comprise illumination means for irradiating white illumination light to the measuring site, excitation light irradiating means for irradiating the excitation light to the measuring site, and imaging means for performing imaging operations for detecting an ordinary image and a fluorescence image. FIG. 10 is a timing chart showing timings, with which imaging operations are performed in conventional fluorescence imaging apparatuses. As illustrated in FIG. 10, in the conventional fluorescence imaging apparatuses, the irradiation of the white light and the irradiation of the excitation light are switched between each other with manual operations or at predetermined intervals, and the fluorescence image or the ordinary image is displayed as a dynamic image on the monitor.

With the conventional fluorescence imaging apparatuses described above, only either one of the ordinary image and the fluorescence image is displayed on the monitor. Therefore, the problems occur in that, for example, when a person, who sees the displayed image, finds the presence of the diseased tissues from the displayed fluorescence image and changes over the imaging operation from the detection of the fluorescence image to the detection of the ordinary image in order to perform treatment, it becomes impossible to find the position of the diseased tissues. In order for the problems described above to be eliminated, there is a strong demand for a fluorescence imaging apparatus, with which both the fluorescence image and the ordinary image are capable of being displayed simultaneously as real-time dynamic images on a monitor.

In order for the dynamic images of the fluorescence image and the ordinary image to be displayed simultaneously on a monitor, it may be considered to provide ordinary imaging means for performing the imaging operation for detecting the ordinary image and fluorescence imaging means for performing the imaging operation for detecting the fluorescence image as two independent means, and to alternately perform operations for irradiating the illumination light and detecting the ordinary image and operations for irradiating the excitation light and detecting the fluorescence image in a time division mode.

However, in order for both the ordinary image and the fluorescence image to be displayed as the dynamic images, it is necessary that the imaging operation for detecting the ordinary image and the imaging operation for detecting the fluorescence image be changed over quickly. In such cases, it is not always possible to utilize a mechanical shutter, and the like. Also, the problems occur in that, when the illumination light is being irradiated to the measuring site and the ordinary image is being detected by the ordinary imaging means, the reflected light of the illumination light also impinges upon the fluorescence imaging means. As a result, the imaging operation for detecting the fluorescence image cannot be performed accurately.

Further, the problems occur in that, when the fluorescence image is being detected by the fluorescence imaging means, the reflected light of the excitation light also impinges upon the ordinary imaging means. As a result, the imaging operation for detecting the ordinary image cannot be performed accurately.

SUMMARY OF THE INVENTION

The primary object of the present invention is to provide a fluorescence imaging apparatus, wherein ordinary imaging means for performing an imaging operation for detecting an ordinary image and fluorescence imaging means for performing an imaging operation for detecting a fluorescence image are provided as two independent means, and a combination of irradiation of illumination light and an imaging operation for detecting the ordinary image and a combination of irradiation of excitation light and an imaging operation for detecting the fluorescence image are performed alternately in a time division mode, such that the imaging operation for detecting the fluorescence image is not adversely affected by reflected light of the illumination light, which reflected light impinges upon the fluorescence imaging means when the imaging operation for detecting the ordinary image is being performed, and such that a sharp fluorescence image is capable of being detected.

Another object of the present invention is to provide a fluorescence imaging apparatus, wherein an imaging operation for detecting an ordinary image is not adversely affected by reflected light of excitation light, which reflected light impinges upon ordinary imaging means when an imaging operation for detecting a fluorescence image is being performed, and a sharp ordinary image is capable of being detected.

The present invention provides a first fluorescence imaging apparatus, comprising:

i) excitation light irradiating means for irradiating excitation light to a measuring site, the excitation light causing the measuring site to produce fluorescence, ii) fluorescence imaging means for performing an imaging operation for detecting a fluorescence image formed with the fluorescence, which has been produced from the measuring site when the excitation light is irradiated to the measuring site, iii) illumination means for irradiating illumination light to the measuring site, iv) ordinary imaging means for performing an imaging operation for detecting an ordinary image formed with reflected light of the illumination light, which reflected light has been reflected by the measuring site when the illumination light is irradiated to the measuring site, and v) control means for controlling operations of the excitation light irradiating means, the fluorescence imaging means, the illumination means, and the ordinary imaging means, such that the imaging operation for detecting the fluorescence image and the imaging operation for detecting the ordinary image are performed alternately, wherein the control means controls such that an operation for throwing off accumulated electric charges is performed before the imaging operation of the fluorescence imaging means is performed and/or before the imaging operation of the ordinary imaging means is performed.

The present invention also provides a second fluorescence imaging apparatus, comprising:

i) excitation light irradiating means for irradiating excitation light to a measuring site, the excitation light causing the measuring site to produce fluorescence, ii) fluorescence imaging means for performing an imaging operation for detecting a fluorescence image formed with the fluorescence, which has been produced from the measuring site when the excitation light is irradiated to the measuring site, iii) illumination means for irradiating illumination light to the measuring site, iv) ordinary imaging means for performing an imaging operation for detecting an ordinary image formed with reflected light of the illumination light, which reflected light has been reflected by the measuring site when the illumination light is irradiated to the measuring site, and v) control means for controlling operations of the excitation light irradiating means, the fluorescence imaging means, the illumination means, and the ordinary imaging means, such that the imaging operation for detecting the fluorescence image and the imaging operation for detecting the ordinary image are performed alternately, wherein the ordinary imaging means is provided with excitation light removing means for removing the excitation light from light impinging upon the ordinary imaging means.

The present invention further provides a third fluorescence imaging apparatus, comprising:

i) excitation light irradiating means for irradiating excitation light to a measuring site, the excitation light causing the measuring site to produce fluorescence, ii) fluorescence imaging means for performing an imaging operation for detecting a fluorescence image formed with the fluorescence, which has been produced from the measuring site when the excitation light is irradiated to the measuring site, iii) illumination means for irradiating illumination light to the measuring site, iv) ordinary imaging means for performing an imaging operation for detecting an ordinary image formed with reflected light of the illumination light, which reflected light has been reflected by the measuring site when the illumination light is irradiated to the measuring site, and v) control means for controlling operations of the excitation light irradiating means, the fluorescence imaging means, the illumination means, and the ordinary imaging means, such that the imaging operation for detecting the fluorescence image and the imaging operation for detecting the ordinary image are performed alternately, wherein the ordinary imaging means is provided with excitation light removing means for removing the excitation light from light impinging upon the ordinary imaging means, and the control means controls such that an operation for throwing off accumulated electric charges is performed before the imaging operation of the fluorescence imaging means is performed.

In the second and third fluorescence imaging apparatuses in accordance with the present invention, the excitation light removing means should preferably be an excitation light cut-off filter for transmitting only light having wavelengths falling within a wavelength region other than the wavelength region of the excitation light.

In the first and third fluorescence imaging apparatuses in accordance with the present invention, the operation for throwing off the accumulated electric charges should preferably be a dummy reading operation.

Also, the first and third fluorescence imaging apparatuses in accordance with the present invention should preferably be modified such that the fluorescence imaging means and/or the ordinary imaging means comprises a substrate and an image sensor formed on the substrate, and the operation for throwing off the accumulated electric charges is an operation for sweeping out unnecessary electric charges toward the substrate direction.

The illumination light is utilized for illuminating the measuring site in order for the ordinary image to be detected. As the illumination light, one of various kinds of light enabling the ordinary image to be detected may be utilized. For example, in cases where a simultaneous mode technique, in which an on-chip color filter is employed, is utilized for the imaging operation for detecting the ordinary image, white light may be utilized as the illumination light. In cases where a surface sequential technique for successively detecting three-color light images is utilized for the imaging operation for detecting the ordinary image, three-color surface sequential light beams, which are irradiated successively, may be utilized as the illumination light.

The dummy reading operation may be one of various operations for reading unnecessary electric charges, which have been accumulated in the imaging means, and preventing the thus read unnecessary electric charges from being subjected to regular signal processing. For example, the dummy reading operation may be a reading operation wherein, after the unnecessary electric charges have been read, writing of a signal, which is formed with the unnecessary electric charges, into a memory is not performed in a subsequent processing circuit. Alternatively, the dummy reading operation may be a reading operation wherein, after the unnecessary electric charges have been read, the unnecessary electric charges are erased to the ground at a subsequent stage.

With the first fluorescence imaging apparatus in accordance with the present invention, the control means for controlling the operations of the excitation light irradiating means, the fluorescence imaging means, the illumination means, and the ordinary imaging means, controls such that the operation for throwing off the accumulated electric charges is performed before the imaging operation of the fluorescence imaging means is performed. Therefore, the electric charges having been accumulated in the fluorescence imaging means due to the reflected light of the illumination light, which reflected light impinges upon the fluorescence imaging means when the imaging operation for detecting the ordinary image is performed, are thrown off before the imaging operation for detecting the fluorescence image is performed. Accordingly, the imaging operation for detecting the fluorescence image is not affected by the electric charges described above, and a sharp fluorescence image is capable of being detected.

Also, with the first fluorescence imaging apparatus in accordance with the present invention, the control means controls such that the operation for throwing off the accumulated electric charges is performed before the imaging operation of the ordinary imaging means is performed. Therefore, the electric charges having been accumulated in the ordinary imaging means due to the reflected light of the excitation light, which reflected light impinges upon the ordinary imaging means when the imaging operation for detecting the fluorescence image is performed, are thrown off before the imaging operation for detecting the ordinary image is performed. Accordingly, the imaging operation for detecting the ordinary image is not affected by the electric charges described above, and a sharp ordinary image is capable of being detected.

With the second fluorescence imaging apparatus in accordance with the present invention, wherein the ordinary imaging means is provided with the excitation light removing means for removing the excitation light from the light impinging upon the ordinary imaging means, the reflected light of the excitation light is capable of being prevented from entering into the ordinary imaging means when the imaging operation for detecting the fluorescence image is performed. Therefore, the imaging operation for detecting the ordinary image is not affected by the reflected light of the excitation light, and a sharp ordinary image is capable of being detected.

Also, in such cases, the fluorescence, which has been produced from the measuring site when the excitation light is irradiated to the measuring site, also impinges upon the ordinary imaging means. However, the light intensity of the fluorescence is lower than the light intensity of the reflected light of the illumination light, which reflected light impinges upon the ordinary imaging means when the imaging operation for detecting the ordinary image is performed. Therefore, little effect occurs upon the imaging operation for detecting the ordinary image.

With the third fluorescence imaging apparatus in accordance with the present invention, the ordinary imaging means is provided with the excitation light removing means for removing the excitation light from the light impinging upon the ordinary imaging means. Also, the control means controls such that the operation for throwing off the accumulated electric charges is performed before the imaging operation of the fluorescence imaging means is performed. Therefore, the reflected light of the excitation light is capable of being prevented from entering into the ordinary imaging means when the imaging operation for detecting the fluorescence image is performed. Also, the electric charges having been accumulated in the fluorescence imaging means due to the reflected light of the illumination light, which reflected light impinges upon the fluorescence imaging means when the imaging operation for detecting the ordinary image is performed, are thrown off before the imaging operation for detecting the fluorescence image is performed. Accordingly, a sharp ordinary image and a sharp fluorescence image are capable of being detected.

With the second and third fluorescence imaging apparatuses in accordance with the present invention, wherein the excitation light removing means is the excitation light cut-off filter for transmitting only light having wavelengths falling within a wavelength region other than the wavelength region of the excitation light, with the simple constitution, the reflected light of the excitation light is capable of being prevented from entering into the ordinary imaging means when the imaging operation for detecting the fluorescence image is performed.

With the first and third fluorescence imaging apparatuses in accordance with the present invention, wherein the operation for throwing off the accumulated electric charges is the dummy reading operation, the reading operation under the control of the control means need not be altered markedly between when the ordinary reading operation is performed and when the dummy reading operation is performed. Therefore, the constitution of the control means is capable of being simplified.

With the first and third fluorescence imaging apparatuses in accordance with the present invention, the fluorescence imaging means and/or the ordinary imaging means may comprise the substrate and the image sensor formed on the substrate, and the operation for throwing off the accumulated electric charges may be the operation for sweeping out the unnecessary electric charges toward the substrate direction. In such cases, the timing, with which the unnecessary electric charges are swept out, is capable of being set arbitrarily. Therefore, the imaging time is capable of being set arbitrarily in accordance with imaging conditions.

DESCRIPTION OF THE PREFERRED EMBODIMENTS

The present invention will hereinbelow be described in further detail with reference to the accompanying drawings.

Figure 1:
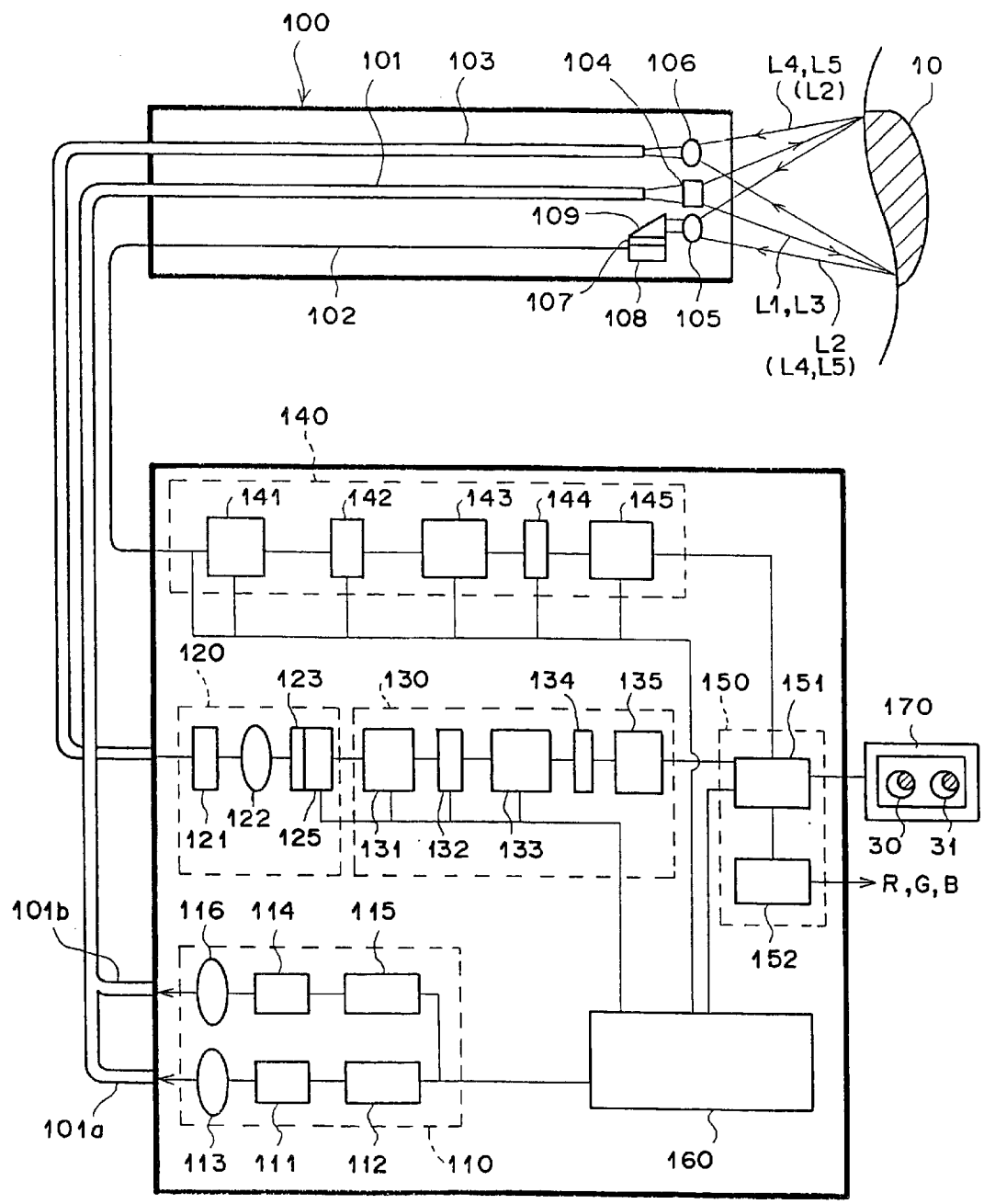
FIG. 1 is a schematic view showing an endoscope system, in which a first embodiment of the fluorescence imaging apparatus in accordance with the present invention is employed.

Firstly, an endoscope system, in which a first embodiment of the fluorescence imaging apparatus in accordance with the present invention is employed, will be described hereinbelow with reference to FIG. 1 to FIG. 4. FIG. 1 is a schematic view showing the endoscope system, in which the first embodiment of the fluorescence imaging apparatus in accordance with the present invention is employed. In the endoscope system, in which the first embodiment of the fluorescence imaging apparatus in accordance with the present invention is employed, illumination light is irradiated to a measuring site, and an ordinary image formed with reflected light of the illumination light is detected by a color charge coupled device (CCD) image sensor, which is located at a leading end of an endoscope. The detected ordinary image is displayed as a color image on a monitor. Also, excitation light is irradiated to the measuring site, the excitation light causing the measuring site to produce fluorescence. The fluorescence produced from the measuring site is two-dimensionally acquired as a fluorescence image and with an image fiber. The fluorescence image is detected by a CCD image sensor combined with a mosaic filter constituted of an array of band-pass filter elements for transmitting only fluorescence components of the fluorescence, which fluorescence components have wavelengths falling within predetermined wavelength regions. The detected fluorescence image is displayed as a pseudo color image on a monitor. An imaging operation for detecting the fluorescence image and an imaging operation for detecting the ordinary image are performed in a time division mode. Also, a dummy reading operation is performed before the imaging operation is performed with each of the CCD image sensors.

The endoscope system, in which the first embodiment of the fluorescence imaging apparatus in accordance with the present invention is employed, comprises an endoscope 100 to be inserted into a region of a patient, which region is considered as being a diseased part, and an illuminating unit 110 provided with light sources for producing white light, which is used when an imaging operation for detecting the ordinary image is to be performed, and the excitation light, which is used when an imaging operation for detecting the fluorescence image is to be performed. The endoscope system also comprises a fluorescence imaging unit 120 for receiving the fluorescence, which is produced from the measuring site in the living body when the measuring site is exposed to the excitation light, and detecting the image of the fluorescence. The endoscope system further comprises a fluorescence image processing unit 130 for performing image processing for displaying the fluorescence image as a pseudo color image in accordance with the ratio between signal intensities of fluorescence components of the fluorescence, which fluorescence components have wavelengths falling within predetermined wavelength regions. The endoscope system still further comprises an ordinary image processing unit 140 for performing image processing for displaying an ordinary image as a color image. The endoscope system also comprises a display image processing unit 150 for superimposing the color image of the ordinary image and the pseudo color image of the fluorescence image one upon the other. The endoscope system further comprises a controller 160, which is connected to the respective units and controls operation timings. The endoscope system still further comprises a monitor 170 for displaying the ordinary image (specifically, the color image of the ordinary image) and the fluorescence image (specifically, the pseudo color image of the fluorescence image), which have been superimposed one upon the other by the display image processing unit 150.

A light guide 101, a CCD cable 102, and an image fiber 103 extend in the endoscope 100 up to a leading end of the endoscope 100. An illuminating lens 104 is located at a leading end of the light guide 101, i.e. at the leading end of the endoscope 100. An objective lens 105 is located at a leading end of the CCD cable 102, i.e. at the leading end of the endoscope 100. The image fiber 103 is constituted of glass fibers, and a converging lens 106 is located at a leading end of the image fiber 103. A CCD image sensor 108 is connected to the leading end of the CCD cable 102. A mosaic filter 107 is combined with the CCD image sensor 108. Also, a prism 109 is mounted on the CCD image sensor 108.

The mosaic filter 107 is a complementary color type of filter, which is constituted of band-pass filter elements arrayed alternately in a mosaic form. The band-pass filter elements transmit light having wavelengths falling within wavelength regions constituting complementary colors with respect to the three primary colors. Each of the band-pass filter elements of the mosaic filter 107 corresponds to one of the pixels in the CCD image sensor 108.

The CCD image sensor 108 is an interline type of CCD image sensor. In the CCD image sensor 108, signal charges, which have been formed from photoelectric conversion performed at a photosensitive section, are read into a transfer section and are then successively fed out from the transfer section.

The light guide 101 comprises a white light guide 101a, which is constituted of a compound glass fiber, and an excitation light guide 101b, which is constituted of a quartz glass fiber. The white light guide 101a and the excitation light guide 101b are bundled together in a cable-like form to constitute the light guide 101. The white light guide 101a and the excitation light guide 101b are connected to the illuminating unit 110. A tail end of the CCD cable 102 is connected to the ordinary image processing unit 140. A tail end of the image fiber 103 is connected to the fluorescence imaging unit 120.

The illuminating unit 110 comprises a white light source 111 for producing white light L1, which is used when the imaging operation for detecting the ordinary image is to be performed, and an electric power source 112, which is electrically connected to the white light source 111. The illuminating unit 110 also comprises a GaN type of semiconductor laser 114 for producing excitation light L3, which is used when the imaging operation for detecting the fluorescence image is to be performed, and an electric power source 115, which is electrically connected to the GaN type of semiconductor laser 114.

The fluorescence imaging unit 120 comprises an excitation light cut-off filter 121 for removing reflected light L5 of the excitation light L3 from the light, which is composed of the fluorescence L4 and the reflected light L5 impinging upon the image fiber 103. The fluorescence imaging unit 120 also comprises a CCD image sensor 125. The CCD image sensor 125 is combined with a mosaic filter 123. The excitation light cut-off filter 121 is a band-pass filter for filtering out light, which has wavelengths falling within a wavelength region of at most 430 nm in the vicinity of the wavelength of the excitation light L3.

Figure 2:
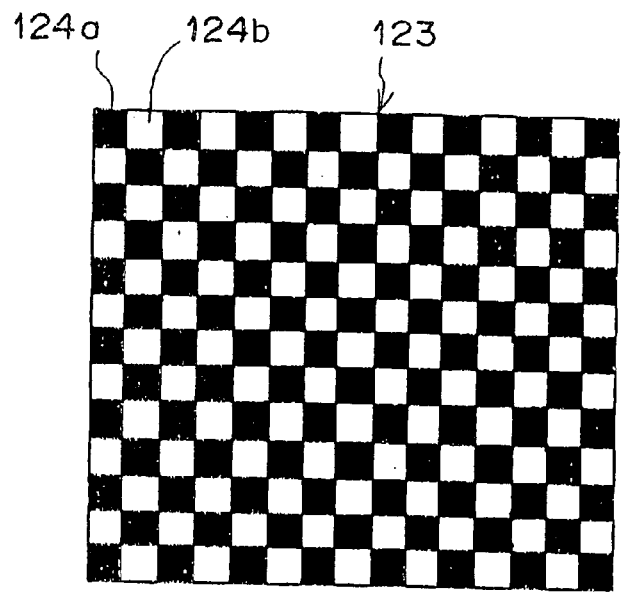
FIG. 2 is a schematic view showing a mosaic filter for a fluorescence image employed in the endoscope system, in which the first embodiment of the fluorescence imaging apparatus in accordance with the present invention is employed.
Figure 3:
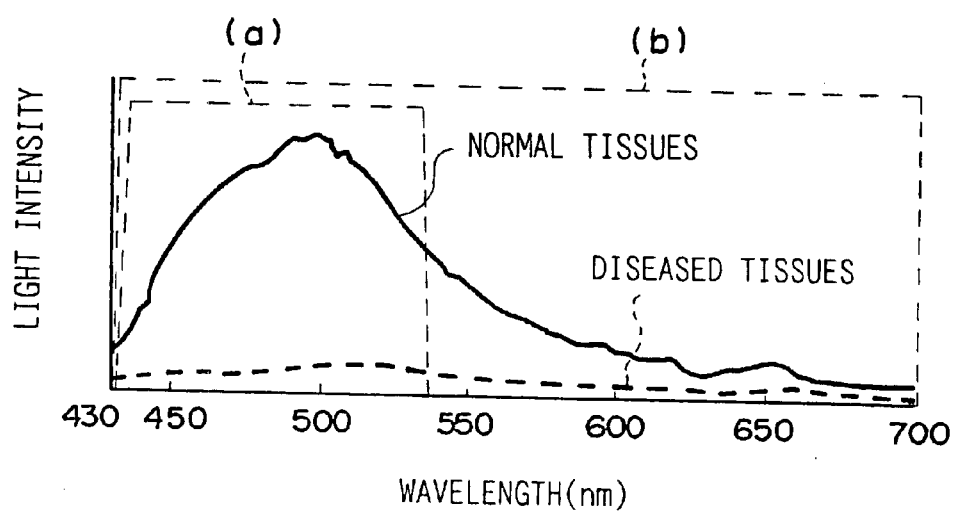
FIG. 3 is a graph showing transmission wavelength regions of band-pass filter elements constituting the mosaic filter for a fluorescence image employed in the endoscope system, in which the first embodiment of the fluorescence imaging apparatus in accordance with the present invention is employed.

As illustrated in FIG. 2, the mosaic filter 123 is constituted of band-pass filter elements 124a, 124a, . . . and band-pass filter elements 124b, 124b, . . . , which are arrayed alternately. The band-pass filter elements 124a, 124a, . . . have transmission characteristics indicated by (a) in FIG. 3, and transmit only light having wavelengths falling within a blue wavelength region. The band-pass filter elements 124b, 124b, . . . have transmission characteristics indicated by (b) in FIG. 3, and transmit light having wavelengths falling within an entire measurement wavelength region. Each of the band-pass filter elements 124a, 124a, . . . and the band-pass filter elements 124b, 124b, . . . corresponds to one of pixels in the CCD image sensor 125.

The CCD image sensor 125 is a frame transfer type of cooled, back exposure CCD image sensor. In the CCD image sensor 125, signal charges, which have been formed from photoelectric conversion performed at a photosensitive section, are transferred into an accumulating section and are then successively fed out from the accumulating section.

The fluorescence image processing unit 130 comprises a signal processing circuit 131 for performing sampling, clamping, blanking, amplification, and the like, on signals, which have been obtained from the CCD image sensor 125, and forming pseudo color image signals from the signal intensity of fluorescence components of the fluorescence, which fluorescence components have wavelengths falling within the blue wavelength region, and the signal intensity of fluorescence components of the fluorescence, which fluorescence components have wavelengths falling within the entire measurement wavelength region. The fluorescence image processing unit 130 also comprises an analog-to-digital converting circuit 132 for digitizing the pseudo color image signals, which have been obtained from the signal processing circuit 131. The fluorescence image processing unit 130 further comprises a fluorescence image memory 133 for storing the digital pseudo color image signals, which have been obtained from the analog-to-digital converting circuit 132. The fluorescence image processing unit 130 still further comprises a digital-to-analog converting circuit 134 for performing digital-to-analog conversion on the pseudo color image signals, which have been received from the fluorescence image memory 133. The fluorescence image processing unit 130 also comprises a fluorescence image encoder 135 for transforming the pseudo color image signals, which have been received from the digital-to-analog converting circuit 134, into video signals.

The ordinary image processing unit 140 comprises a signal processing circuit 141 for forming color image signals from the ordinary image, which has been detected by the CCD image sensor 108. The ordinary image processing unit 140 also comprises an analog-to-digital converting circuit 142 for digitizing the color image signals, which have been obtained from the signal processing circuit 141. The ordinary image processing unit 140 further comprises an ordinary image memory 143 for storing the digital color image signals, which have been obtained from the analog-to-digital converting circuit 142. The ordinary image processing unit 140 still further comprises a digital-to-analog converting circuit 144 for performing digital-to-analog conversion on the color image signals, which have been received from the ordinary image memory 143. The ordinary image processing unit 140 also comprises an ordinary image encoder 145 for transforming the color image signals, which have been received from the digital-to-analog converting circuit 144, into video signals.

The display image processing unit 150 comprises a super imposer 151 for superimposing the pseudo color image signals, which have been received from the fluorescence image encoder 135, and the color image signals, which have been received from the ordinary image encoder 145, one upon the other, and feeding out the thus obtained image signals as the display signals. The display image processing unit 150 also comprises an RGB decoder 152 for transforming the display signals, which are the video signals, into R, G, and B display signals.

How the endoscope system, in which the first embodiment of the fluorescence imaging apparatus in accordance with the present invention is employed, operates will be described hereinbelow. Firstly, how the endoscope system operates when an ordinary image is to be displayed and when a fluorescence image is to be displayed will be described hereinbelow. Thereafter, operation timings, with which the imaging operation for detecting the ordinary image and the imaging operation for detecting the fluorescence image are performed in the time division mode, and operations at the time of the change-over between the imaging operations will be described.

Firstly, how the endoscope system operates when an ordinary image is to be displayed will be described hereinbelow. When an ordinary image is to be displayed, the electric power source 112 for the white light source 111 is driven in accordance with a control signal fed from the controller 160, and the white light L1 is produced by the white light source 111. The white light L1 passes through a lens 113 and impinges upon the white light guide 101a. The white light L1 is guided through the white light guide 101a to the leading end of the endoscope 100, passes through the illuminating lens 104, and is irradiated to a measuring site 10. The white light L1 is reflected as reflected light L2 from the measuring site 10. The reflected light L2 is converged by the objective lens 105 and reflected by the prism 109. The reflected light L2 then passes through the mosaic filter 107 and is received by the photosensitive section of the CCD image sensor 108. Signal charges, which have been formed in accordance with light intensities and from photoelectric conversion performed at the photosensitive section, are shifted into the transfer section and are then successively fed into the signal processing circuit 141 of the ordinary image processing unit 140.

In the signal processing circuit 141, the processes, such as correlative double sampling, clamping, blanking, and amplification, are performed on the signals having been obtained from the CCD image sensor 108. Thereafter, the resulting signals are subjected to separation for separating a luminance signal and chrominance signals from one another. Thereafter, a luminance signal Y1 and color difference signals R1–Y1 and B1–Y1, which are color image signals, are calculated.

The color image signals (i.e., the luminance signal Y1 and the color difference signals R1–Y1 and B1–Y1), which are made up of color image signal components corresponding to respective pixels and have been obtained from the signal processing circuit 141, are digitized by the analog-to-digital converting circuit 142. The thus obtained luminance signal Y1 is stored in a luminance signal storage area of the ordinary image memory 143. The color difference signals R1–Y1 and B1–Y1 are stored in color difference signal storage areas of the ordinary image memory 143.

In accordance with a display timing, the color image signals (i.e., the luminance signal Y1 and the color difference signals R1–Y1 and B1–Y1) having been stored in the ordinary image memory 143 are subjected to the digital-to-analog conversion in the digital-to-analog converting circuit 144 and transformed by the ordinary image encoder 145 into predetermined video signals. The thus obtained video signals are fed into the superimposer 151 and superimposed upon the pseudo color image signals, which are obtained in the manner described later. The superimposed video signals are fed into the monitor 170 and the RGB decoder 152. How the monitor 170 and the RGB decoder 152 operate will be described later.

How the endoscope system, in which the first embodiment of the fluorescence imaging apparatus in accordance with the present invention is employed, operates when a fluorescence image is to be displayed will be described hereinbelow.

When a fluorescence image is to be displayed, the electric power source 115 for the GaN type of semiconductor laser 114 is driven in accordance with a control signal fed from the controller 160, and the excitation light L3 having a wavelength of 410 nm is produced by the GaN type of semiconductor laser 114. The excitation light L3 passes through a lens 116 and impinges upon the excitation light guide 101b. The excitation light L3 is guided through the excitation light guide 101b to the leading end of the endoscope 100, passes through the illuminating lens 104, and is irradiated to the measuring site 10.

When the measuring site 10 is exposed to the excitation light L3, the fluorescence L4 is produced from the measuring site 10. The fluorescence L4 and the reflected light L5 of the excitation light L3 are converged by the converging lens 106 and impinge upon the leading end of the image fiber 103. The fluorescence L4 and the reflected light L5 then pass through the image fiber 103 and impinge upon the fluorescence imaging unit 120. The reflected light L5 is filtered out by the excitation light cut-off filter 121, and only the fluorescence L4 impinges upon a lens 122. The fluorescence L4, which has been converged by the lens 122, passes through the mosaic filter 123 combined with the CCD image sensor 125 and is then received by the CCD image sensor 125. Signal charges, which have been formed in accordance with light intensities and from photoelectric conversion performed at the photosensitive section of the CCD image sensor 125, are transferred into the accumulating section and are then successively fed into the signal processing circuit 131 of the fluorescence image processing unit 130.

In the signal processing circuit 131, the processes, such as correlative double sampling, clamping, blanking, and amplification, are performed on the signals having been obtained from the CCD image sensor 125. The signals having been obtained from the processes are fed out as two-dimensional signals. Thereafter, with respect to each pixel, color difference matrix operations are performed by utilizing a signal intensity B2 of the fluorescence components of the fluorescence L4, which fluorescence components have wavelengths falling within the blue wavelength region and have passed through the band-pass filter elements 124a, 124a, . . . and a signal intensity W2 of the fluorescence components of the fluorescence L4, which fluorescence components have wavelengths falling within the entire measurement wavelength region and have passed through the band-pass filter elements 124b, 124b, . . . Each of the color difference matrix operations is performed by utilizing the signal intensities corresponding to pixels adjacent to each pixel. In this manner, a pseudo luminance signal Y2 and pseudo color difference signals R2–Y2 and B2–Y2, which act as the pseudo color image signals, are calculated.

The pseudo color image signals (i.e., the pseudo luminance signal Y2 and the pseudo color difference signals R2–Y2 and B2–Y2), which are made up of pseudo color image signal components corresponding to respective pixels and have been obtained from the signal processing circuit 131, are digitized by the analog-to-digital converting circuit 132. The thus obtained pseudo luminance signal Y2 is stored in a luminance signal storage area of the fluorescence image memory 133. Also, the thus obtained pseudo color difference signals R2–Y2 and B2–Y2 are stored in color difference signal storage areas of the fluorescence image memory 133. In accordance with the display timing, the pseudo color image signals (i.e., the pseudo luminance signal Y2 and the pseudo color difference signals R2–Y2 and B2–Y2) having been stored in the fluorescence image memory 133 are subjected to the digital-to-analog conversion in the digital-to-analog converting circuit 134 and transformed by the fluorescence image encoder 135 into predetermined video signals. The thus obtained video signals are fed from the fluorescence image encoder 135 into the superimposer 151. In the superimposer 151, the pseudo color image signals are superimposed upon the color image signals (i.e., the luminance signal Y1 and the color difference signals R1–Y1 and B1–Y1), which represent the ordinary image and have been received from the ordinary image encoder 145. The thus obtained video signals are fed into the monitor 170 and the RGB decoder 152.

The monitor 170 transforms the color image signals and the pseudo color image signals, which have been received as the video signals, and reproduces an ordinary image 30 and a fluorescence image 31 from the image signals having been obtained from the transform. The fluorescence image 31 is displayed with a pseudo color, such that the display color varies in accordance with the ratio between the signal intensity W2 of the fluorescence components, which have wavelengths falling within the entire measurement wavelength region, and the signal intensity B2 of the fluorescence components, which have wavelengths falling within the blue wavelength region. The tint of the pseudo color of the fluorescence image 31 is determined by coefficients in matrix operation formulas employed in the signal processing circuit 131.

In the RGB decoder 152, the color signals R, G, and B representing the ordinary image and the color signals R, G, and B representing the fluorescence image are inversely transformed from the color image signals and the pseudo color image signals, which have been superimposed one upon the other. The color signals R, G, and B are fed into a device (not shown) capable of directly receiving the color signals, such as a printer or an image processing unit. The series of operations described above are controlled by the controller 160.

The operation timings, with which the imaging operation for detecting the ordinary image and the imaging operation for detecting the fluorescence image are performed in the time division mode, and operations at the time of the change-over between the imaging operations will be described hereinbelow.

Figure 4:
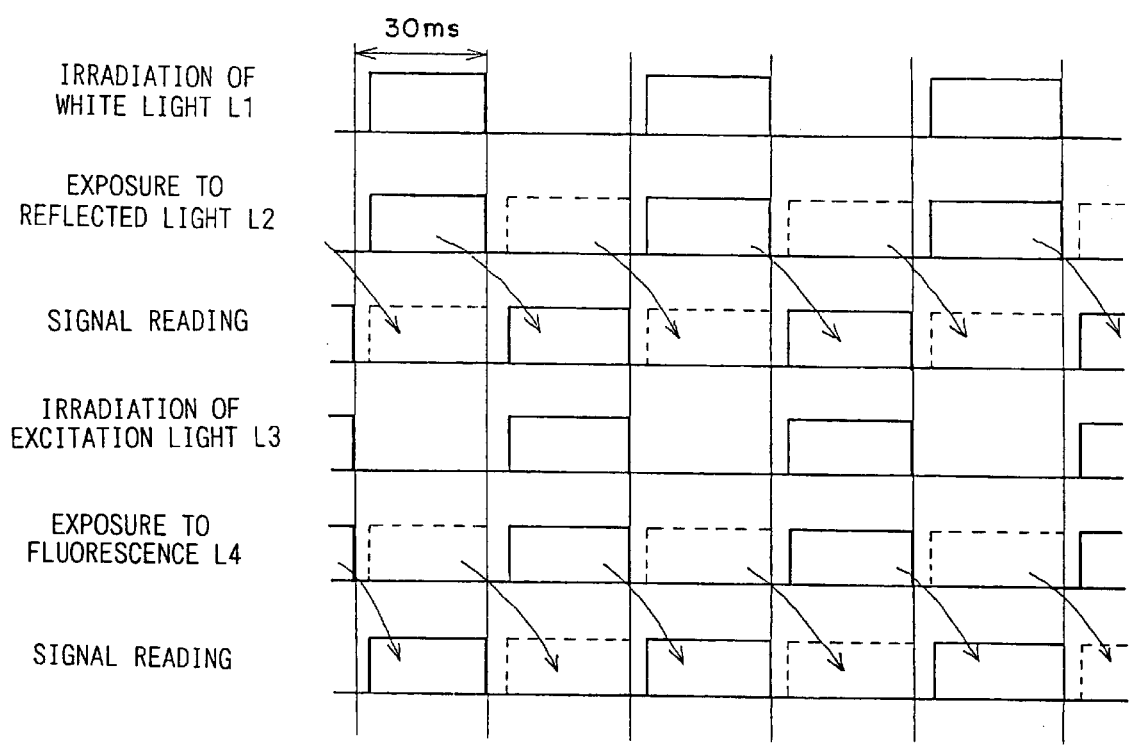
FIG. 4 is a timing chart employed in the endoscope system, in which the first embodiment of the fluorescence imaging apparatus in accordance with the present invention is employed.

The imaging operation for detecting the fluorescence image and the imaging operation for detecting the ordinary image are performed in accordance with a timing chart illustrated in FIG. 4. As illustrated in FIG. 4, the irradiation of the white light L1 and the exposure of the CCD image sensor 108 to the reflected light L2 are performed synchronously every 60 ms for a period slightly shorter than 30 ms. Thereafter, the signal charges, which have been accumulated at the photosensitive section of the CCD image sensor 108 during the exposure period, are shifted into the transfer section. The signal charges, which have been shifted into the transfer section, are read successively during a period, in which the irradiation of the white light L1 is ceased. The signal charges having thus been read are fed out into the signal processing circuit 141 of the ordinary image processing unit 140.

Also, the imaging operation for detecting the fluorescence image is performed during the period, in which the irradiation of the white light L1 is ceased. As in the imaging operation for detecting the ordinary image, the irradiation of the excitation light L3 and the exposure of the CCD image sensor 125 to the fluorescence L4 are performed synchronously every 60 ms for a period slightly shorter than 30 ms. The reflected light L5 of the excitation light L3 is filtered out by the excitation light cut-off filter 121 located in the fluorescence imaging unit 120. Therefore, the reflected light L5 of the excitation light L3 does not impinge upon the CCD image sensor 125. The signal charges, which have been accumulated at the photosensitive section of the CCD image sensor 125 during the exposure period, are shifted into the accumulating section. The signal charges, which have been shifted into the accumulating section, are read successively during a period, in which the irradiation of the excitation light L3 is ceased. The signal charges having thus been read are fed out into the signal processing circuit 131 of the fluorescence image processing unit 130.

As described above, the imaging operation for detecting the fluorescence image and the imaging operation for detecting the ordinary image are performed alternately in the time division mode. Therefore, as indicated by the broken line in a fifth row in FIG. 4, at the time of the imaging operation for detecting the ordinary image, the reflected light L2 of the white light L1 impinges upon the photosensitive section of the CCD image sensor 125 for detecting the fluorescence image and is subjected to photoelectric conversion. As a result, unnecessary signal charges are accumulated at the photosensitive section of the CCD image sensor 125. However, before the irradiation of the excitation light L3 is performed, the unnecessary signal charges are processed with the dummy reading operation.

Specifically, when the irradiation of the white light L1 is completed, as in the cases of the ordinary signal charges, the unnecessary signal charges described above are shifted into the transfer section. The unnecessary signal charges, which have been shifted into the transfer section, are read successively from the transfer section and fed into the signal processing circuit 131 of the fluorescence image processing unit 130. The unnecessary signal charges are subjected to signal processing in the signal processing circuit 131 and are then subjected to the analog-to-digital conversion in the analog-to-digital converting circuit 132. However, in this case, the controller 160 controls so as to set the fluorescence image memory 133 in a writing disabling state. Therefore, the unnecessary signal charges are not stored in the fluorescence image memory 133.

With the dummy reading operation described above, before the irradiation of the excitation light L3 is begun, the unnecessary signal charges having been accumulated in the photosensitive section of the CCD image sensor 125 have been shifted into the transfer section. Therefore, adverse effects do not occur on the imaging operation for detecting the fluorescence image. Also, before the normal signal charges having been accumulated due to the fluorescence L4 are shifted into the transfer section, the unnecessary signal charges having been shifted into the transfer section have been fed out into the signal processing circuit 131 of the fluorescence image processing unit 130. Therefore, no problems occur with the shifting operation.

As described above, the unnecessary signal charges, which have been accumulated in the CCD image sensor 125 for the detection of the fluorescence image due to the reflected light L2 of the white light L1 impinging upon the CCD image sensor 125 at the time of the imaging operation for detecting the ordinary image, are erased with the dummy reading operation before the imaging operation for detecting the fluorescence image is performed. Therefore, adverse effects do not occur on the imaging operation for detecting the fluorescence image, and a sharp fluorescence image is capable of being detected.

Also, as indicated by the broken line in a second row in FIG. 4, at the time of the imaging operation for detecting the fluorescence image, the fluorescence L4 and the reflected light L5 of the excitation light L3 impinge upon the photosensitive section of the CCD image sensor 108 for detecting the ordinary image and are subjected to photoelectric conversion. As a result, unnecessary signal charges are accumulated at the photosensitive section of the CCD image sensor 108. However, before the irradiation of the white light L1 is performed, the unnecessary signal charges are processed with the dummy reading operation.

Specifically, when the irradiation of the excitation light L3 is completed, as in the cases of the ordinary signal charges, the unnecessary signal charges described above are shifted into the transfer section. The unnecessary signal charges, which have been shifted into the transfer section, are fed out from the transfer section and into the signal processing circuit 141 of the ordinary image processing unit 140. The unnecessary signal charges are subjected to signal processing in the signal processing circuit 141 and are then subjected to the analog-to-digital conversion in the analog-to-digital converting circuit 142. However, in this case, the controller 160 controls so as to set the ordinary image memory 143 in a writing disabling state. Therefore, the unnecessary signal charges are not stored in the ordinary image memory 143.

With the dummy reading operation described above, before the irradiation of the white light L1 is begun after the completion of the irradiation of the excitation light L3, the unnecessary signal charges having been accumulated in the photosensitive section of the CCD image sensor 108 have been shifted into the transfer section. Therefore, adverse effects do not occur on the receiving of the reflected light L2 of the white light L1. Also, before the normal signal charges having been accumulated due to the reflected light L2 of the white light L1 are shifted into the transfer section, the unnecessary signal charges having been shifted into the transfer section have been fed out into the signal processing circuit 141 of the ordinary image processing unit 140. Therefore, no problems occur with the shifting operation.

As described above, the unnecessary signal charges, which have been accumulated in the CCD image sensor 108 for the detection of the ordinary image due to the reflected light L5 of the excitation light L3 impinging upon the CCD image sensor 108 at the time of the imaging operation for detecting the fluorescence image, are erased with the dummy reading operation before the imaging operation for detecting the ordinary image is performed. Therefore, adverse effects do not occur on the imaging operation for detecting the ordinary image, and a sharp ordinary image is capable of being detected.

Further, with the embodiment described above, as the operation for throwing off the accumulated electric charges, the dummy reading operation is performed. Therefore, the reading operation under the control of the controller 160 need not be altered markedly between when the ordinary reading operation is performed and when the dummy reading operation is performed. Accordingly, the constitution of the controller 160 is capable of being simplified.

Figure 5:
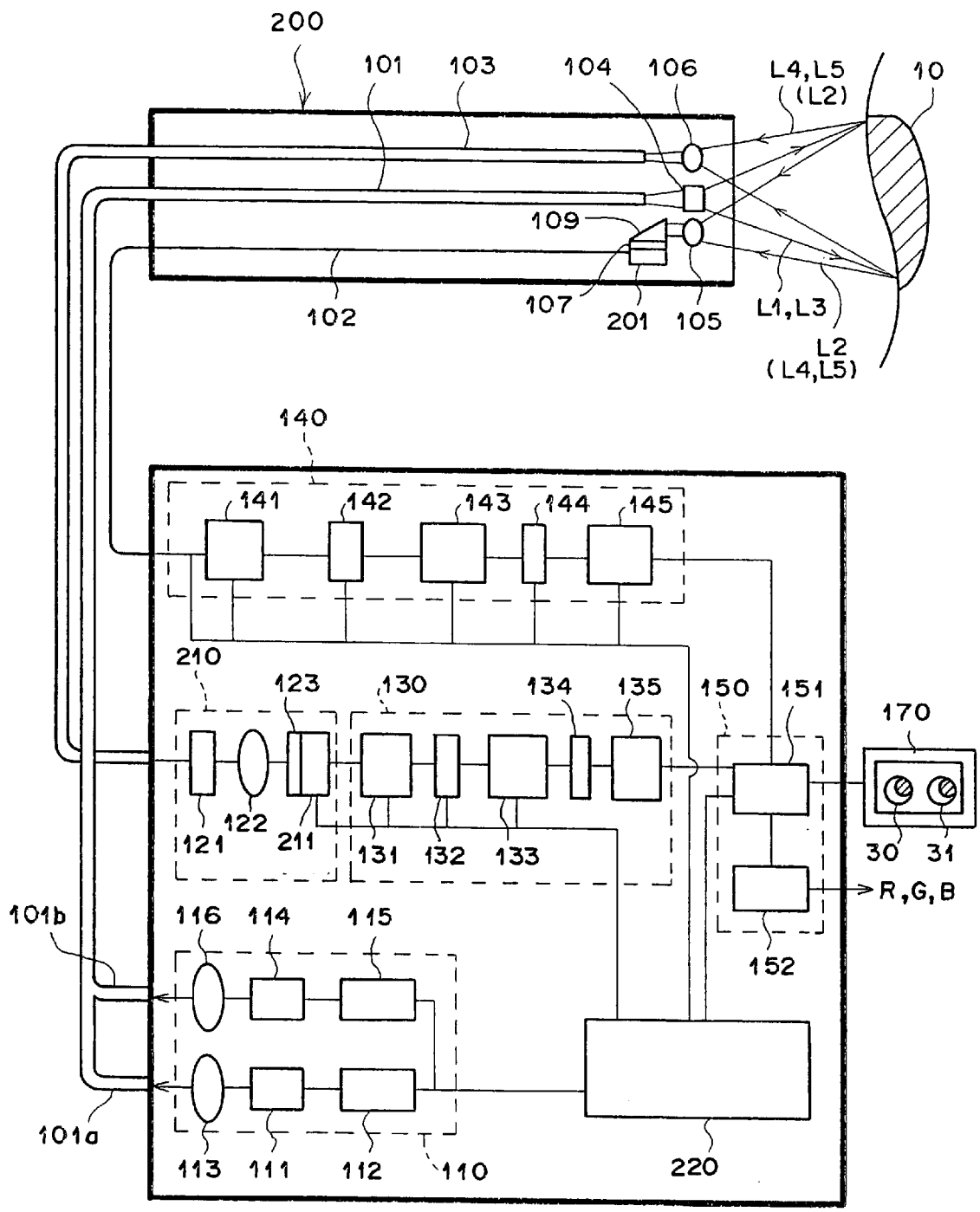
FIG. 5 is a schematic view showing an endoscope system, in which a second embodiment of the fluorescence imaging apparatus in accordance with the present invention is employed.

An endoscope system, in which a second embodiment of the fluorescence imaging apparatus in accordance with the present invention is employed, will be described hereinbelow with reference to FIG. 5 and FIG. 6. FIG. 5 is a schematic view showing the endoscope system, in which the second embodiment of the fluorescence imaging apparatus in accordance with the present invention is employed. In the endoscope system, in which the second embodiment of the fluorescence imaging apparatus in accordance with the present invention is employed, illumination light is irradiated to a measuring site, and an ordinary image formed with reflected light of the illumination light is detected by a color CCD image sensor, which is located at a leading end of an endoscope. The detected ordinary image is displayed as a color image on a monitor. Also, excitation light is irradiated to the measuring site, the excitation light causing the measuring site to produce fluorescence. The fluorescence produced from the measuring site is two-dimensionally acquired as a fluorescence image and with an image fiber. The fluorescence image is detected by a CCD image sensor combined with a mosaic filter constituted of an array of band-pass filter elements for transmitting only fluorescence components of the fluorescence, which fluorescence components have wavelengths falling within predetermined wavelength regions. The detected fluorescence image is displayed as a pseudo color image on a monitor. An imaging operation for detecting the fluorescence image and an imaging operation for detecting the ordinary image are performed in a time division mode. Also, an operation for sweeping out unnecessary electric charges toward a substrate direction is performed before the imaging operation is performed with each of the CCD image sensors.

The endoscope system, in which the second embodiment of the fluorescence imaging apparatus in accordance with the present invention is employed, comprises an endoscope 200 to be inserted into a region of a patient, which region is considered as being a diseased part, and the illuminating unit 110 provided with light sources for producing white light, which is used when an imaging operation for detecting the ordinary image is to be performed, and the excitation light, which is used when an imaging operation for detecting the fluorescence image is to be performed. The endoscope system also comprises a fluorescence imaging unit 210 for receiving the fluorescence, which is produced from the measuring site in the living body when the measuring site is exposed to the excitation light, and detecting the image of the fluorescence. The endoscope system further comprises the fluorescence image processing unit 130 for performing image processing for displaying the fluorescence image as a pseudo color image in accordance with the ratio between signal intensities of fluorescence components of the fluorescence, which fluorescence components have wavelengths falling within predetermined wavelength regions. The endoscope system still further comprises the ordinary image processing unit 140 for performing image processing for displaying an ordinary image as a color image. The endoscope system also comprises the display image processing unit 150 for superimposing the color image of the ordinary image and the pseudo color image of the fluorescence image one upon the other. The endoscope system further comprises a controller 220, which is connected to the respective units and controls operation timings. The endoscope system still further comprises the monitor 170 for displaying the ordinary image (specifically, the color image of the ordinary image) and the fluorescence image (specifically, the pseudo color image of the fluorescence image), which have been superimposed one upon the other by the display image processing unit 150. In FIG. 5, similar elements are numbered with the same reference numerals with respect to FIG. 1.

The light guide 101, the CCD cable 102, and the image fiber 103 extend in the endoscope 200 up to a leading end of the endoscope 200. A CCD image sensor 201 is connected to the leading end of the CCD cable 102. The mosaic filter 107 is combined with the CCD image sensor 201. Also, the prism 109 is mounted on the CCD image sensor 201.

The CCD image sensor 201 is the interline type of CCD image sensor. In the CCD image sensor 201, signal charges, which have been formed from photoelectric conversion performed at a photosensitive section, are shifted into a transfer section and are then successively fed out from the transfer section. Also, the CCD image sensor 201 is provided with a vertical overflow drain structure, in which surplus electric charges beyond a saturation level are drained into a substrate of the CCD image sensor 201. Further, with the application of a sweeping-out pulse, the electric charges having been accumulated in the photosensitive section are capable of being swept out via the drain structure toward the substrate direction.

The fluorescence imaging unit 210 comprises the excitation light cut-off filter 121 and a CCD image sensor 211. The CCD image sensor 211 is combined with the mosaic filter 123. The CCD image sensor 211 is the interline type of CCD image sensor. In the CCD image sensor 211, signal charges, which have been formed from photoelectric conversion performed at a photosensitive section, are shifted into a transfer section and are then successively fed out from the transfer section. Also, as in the CCD image sensor 201, the CCD image sensor 211 is provided with the vertical overflow drain structure. With the application of a sweeping-out pulse, the electric charges having been accumulated in the photosensitive section are capable of being swept out via the drain structure toward the substrate direction. The operations of the respective units are controlled by the controller 220.

How the endoscope system, in which the second embodiment of the fluorescence imaging apparatus in accordance with the present invention is employed, operates will be described hereinbelow. Firstly, how the endoscope system operates when an ordinary image is to be displayed and when a fluorescence image is to be displayed will be described briefly. Thereafter, operation timings, with which the imaging operation for detecting the ordinary image and the imaging operation for detecting the fluorescence image are performed in the time division mode, and operations at the time of the change-over between the imaging operations will be described.

When an ordinary image is to be displayed, the reflected light L2 is converged by the objective lens 105 and reflected by the prism 109. The reflected light L2 then passes through the mosaic filter 107 and is received by the photosensitive section of the CCD image sensor 201. Signal charges, which have been formed in accordance with light intensities and from photoelectric conversion performed at the photosensitive section, are shifted into the transfer section and are then successively fed into the signal processing circuit 141 of the ordinary image processing unit 140.

When a fluorescence image is to be displayed, the fluorescence L4, which is produced from the measuring site 10 when the measuring site 10 is exposed to the excitation light L3, and the reflected light L5 of the excitation light L3 pass through the image fiber 103 and impinge upon the excitation light cut-off filter 121 of the fluorescence imaging unit 210. The reflected light L5 of the excitation light L3 is filtered out by the excitation light cut-off filter 121. The fluorescence L4, which has been converged by the lens 122, passes through the mosaic filter 123 combined with the CCD image sensor 211 and is then received by the CCD image sensor 211. Signal charges, which have been formed in accordance with light intensities and from photoelectric conversion performed at the photosensitive section of the CCD image sensor 211, are shifted into the transfer section and are then successively fed from the transfer section into the signal processing circuit 131 of the fluorescence image processing unit 130.

The operations in the signal processing circuit 141 and the signal processing circuit 131 and the subsequent operations are performed in the same manner as that in the first embodiment described above.

The operation timings, with which the imaging operation for detecting the ordinary image and the imaging operation for detecting the fluorescence image are performed in the time division mode, and operations at the time of the change-over between the imaging operations will be described hereinbelow.

Figure 6:
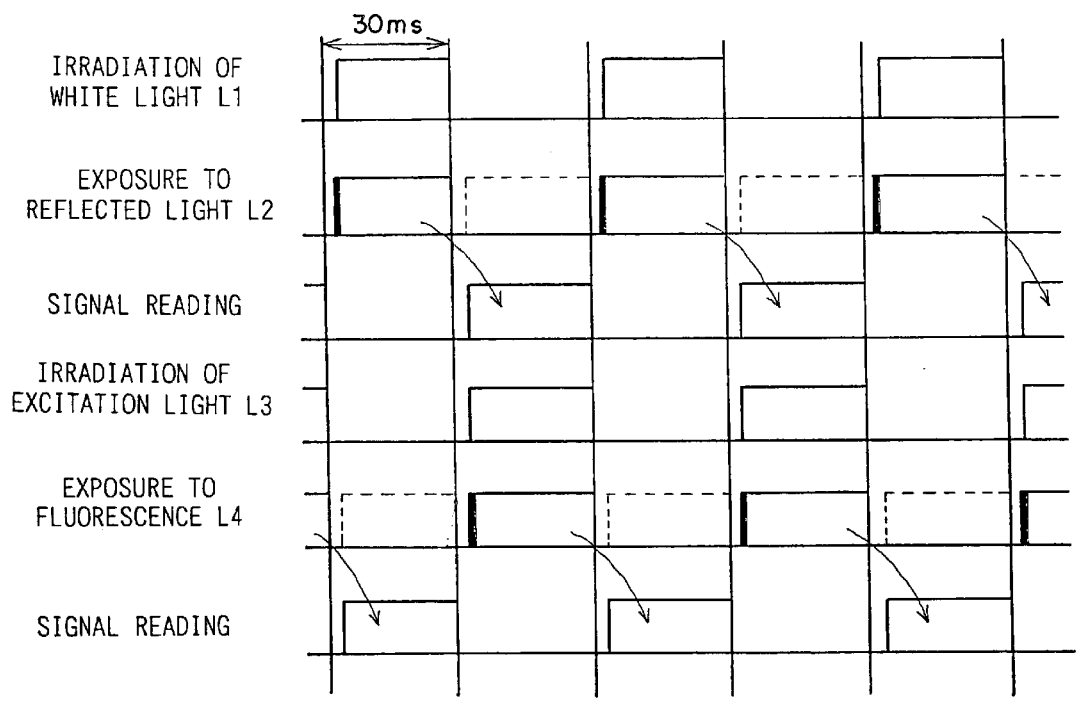
FIG. 6 is a timing chart employed in the endoscope system, in which the second embodiment of the fluorescence imaging apparatus in accordance with the present invention is employed.

The imaging operation for detecting the fluorescence image and the imaging operation for detecting the ordinary image are performed in accordance with a timing chart illustrated in FIG. 6. As illustrated in FIG. 6, the imaging operation for detecting the ordinary image is performed with the same operation timing as the operation timing in the first embodiment described above. The signal charges, which have been accumulated at the photosensitive section of the CCD image sensor 201 during the exposure period, are shifted into the transfer section. The signal charges, which have been shifted into the transfer section, are fed out into the signal processing circuit 141 of the ordinary image processing unit 140 during a period, in which the irradiation of the white light L1 is ceased.

Also, the imaging operation for detecting the fluorescence image is performed with the same operation timing as the operation timing in the first embodiment described above. The signal charges, which have been accumulated at the photosensitive section of the CCD image sensor 211 during the exposure period, are shifted into the transfer section. The signal charges, which have been shifted into the transfer section, are fed out into the signal processing circuit 131 of the fluorescence image processing unit 130 during a period, in which the irradiation of the excitation light L3 is ceased.

As described above, the imaging operation for detecting the fluorescence image and the imaging operation for detecting the ordinary image are performed alternately in the time division mode. Therefore, as indicated by the broken line in a fifth row in FIG. 6, when the white light L1 is being irradiated to the measuring site 10, unnecessary signal charges are accumulated at the photosensitive section of the CCD image sensor 211 for detecting the fluorescence image. In this case, the controller 220 controls such that, when the irradiation of the white light L1 is completed, the unnecessary signal charges having been accumulated at the photosensitive section are not shifted into the transfer section. Immediately before the irradiation of the excitation light L3 is begun, the controller 220 applies a sweeping-out pulse to the CCD image sensor 211.

In the CCD image sensor 211, when the sweeping-out pulse is applied, the unnecessary signal charges are drained toward the substrate direction and are erased. Therefore, when the irradiation of the excitation light L3 is begun, the unnecessary signal charges having been accumulated at the photosensitive section of the CCD image sensor 211 have been erased. Accordingly, no problems occur with the receiving of the fluorescence L4.

As described above, the unnecessary signal charges, which have been accumulated in the CCD image sensor 211 for the detection of the fluorescence image due to the reflected light L2 of the white light L1 impinging upon the CCD image sensor 211 at the time of the imaging operation for detecting the ordinary image, are drained toward the substrate direction and erased prior to the imaging operation for detecting the fluorescence image. Therefore, adverse effects do not occur on the imaging operation for detecting the fluorescence image, and a sharp fluorescence image is capable of being detected.

Also, as indicated by the broken line in a second row in FIG. 6, at the time of the imaging operation for detecting the fluorescence image, unnecessary signal charges due to the reflected light L5 of the excitation light L3 are accumulated at the photosensitive section of the CCD image sensor 201 for detecting the ordinary image. In this case, the controller 220 controls such that, when the irradiation of the excitation light L3 is completed, the unnecessary signal charges having been accumulated at the photosensitive section are not shifted into the transfer section. Immediately before the irradiation of the white light L1 is begun, the controller 220 applies a sweeping-out pulse to the CCD image sensor 201.

In the CCD image sensor 201, when the sweeping-out pulse is applied, the unnecessary signal charges are drained toward the substrate direction and are erased. Therefore, when the irradiation of the white light L1 is begun, the unnecessary signal charges having been accumulated at the photosensitive section of the CCD image sensor 201 have been erased. Accordingly, no problems occur with the receiving of the reflected light L2 of the white light L1.

Further, with the second embodiment described above, as the operation for throwing off the accumulated electric charges, the operation for sweeping out unnecessary electric charges toward the substrate direction is performed. Therefore, the timing, with which the unnecessary signal charges are swept out, is capable of being set arbitrarily.

Accordingly, the imaging time is capable of being set arbitrarily in accordance with imaging conditions.

Figure 11:
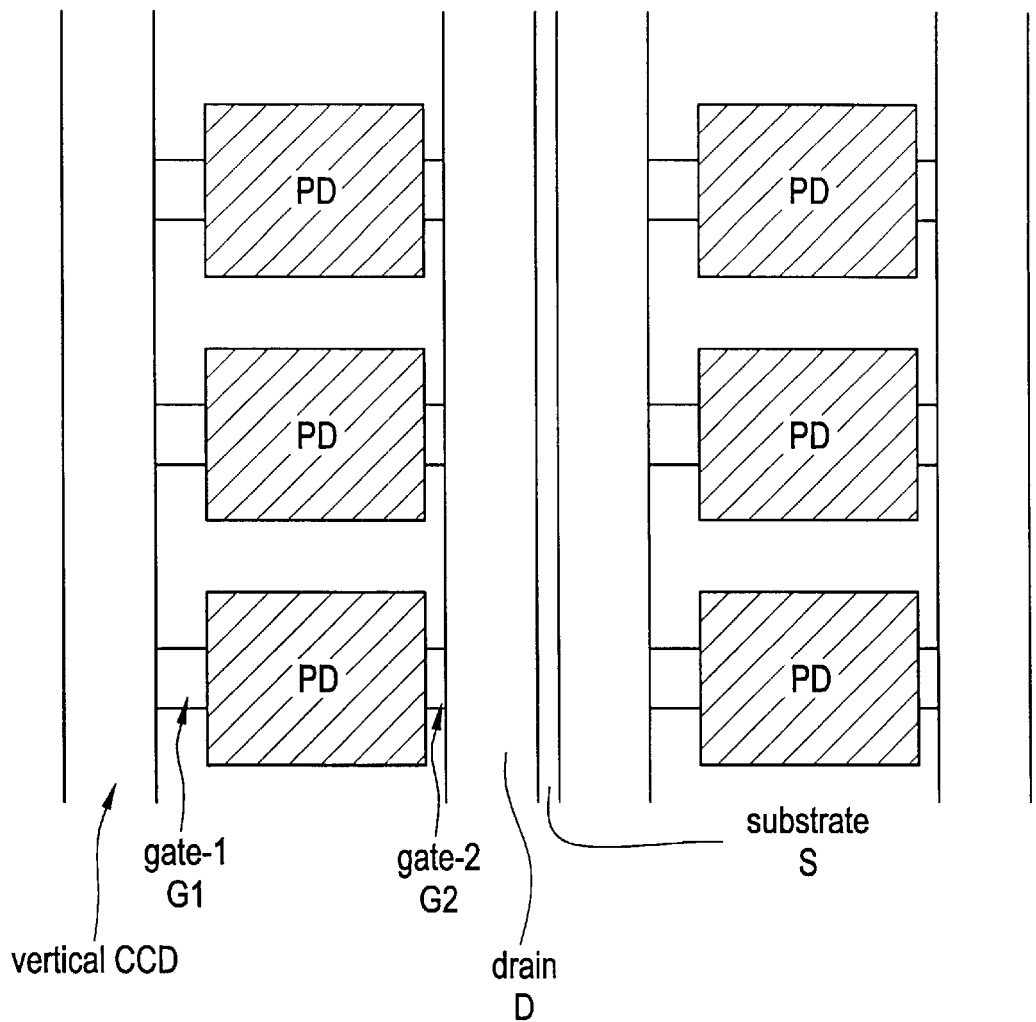
FIG. 11 illustrates an imaging device structure according to an exemplary embodiment of the invention.

Referring to FIG. 11, to sweep out unnecessary electric charges toward a substrate S the electric potential of gate G2 is lowered and the electric charges in the detector elements PD are transferred to the drain D. The electric charges in the drain are transferred to the substrate.

Figure 7:
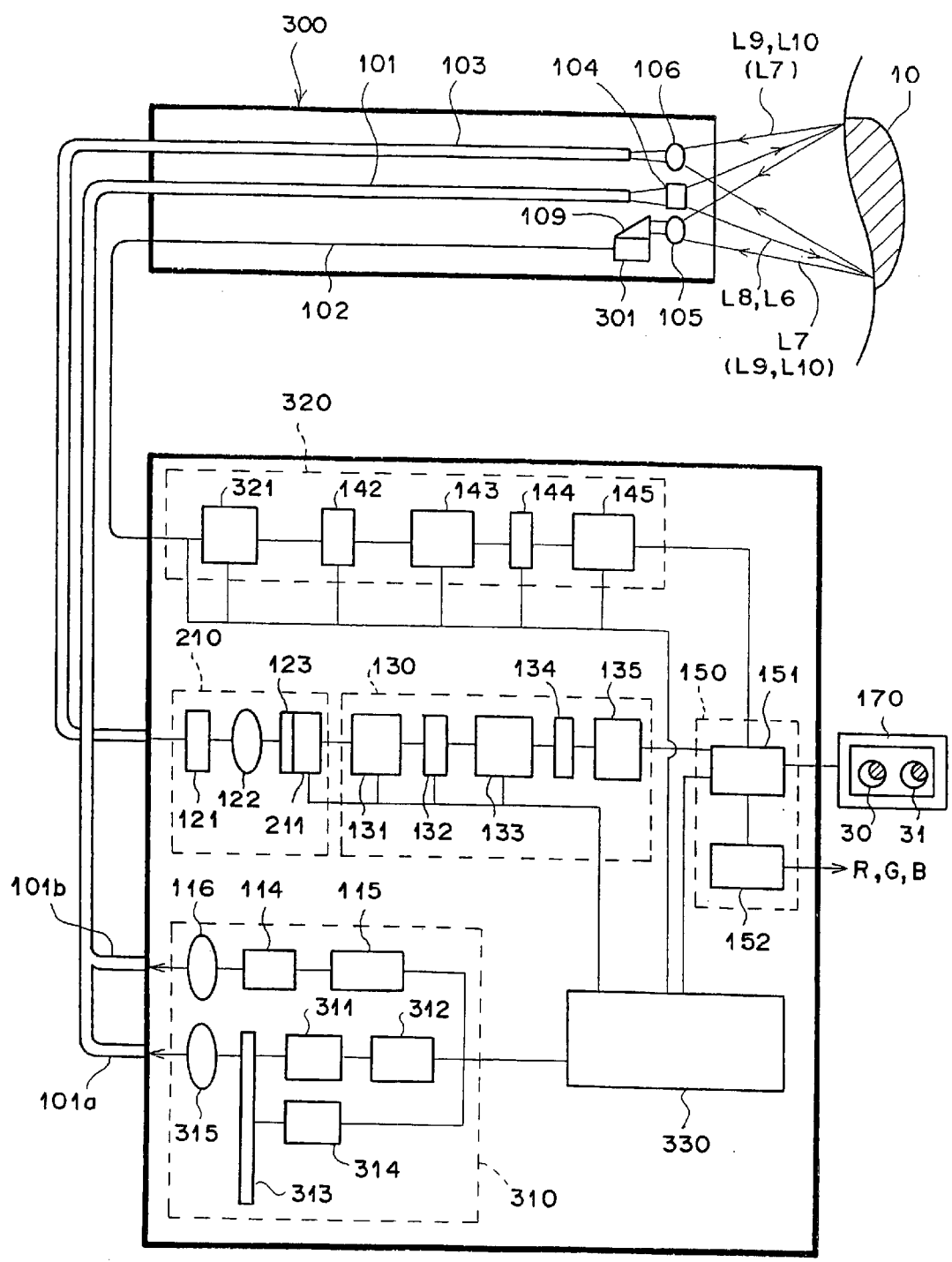
FIG. 7 is a schematic view showing an endoscope system, in which a third embodiment of the fluorescence imaging apparatus in accordance with the present invention is employed.

An endoscope system, in which a third embodiment of the fluorescence imaging apparatus in accordance with the present invention is employed, will be described hereinbelow with reference to FIG. 7 and FIG. 8. FIG. 7 is a schematic view showing the endoscope system, in which the third embodiment of the fluorescence imaging apparatus in accordance with the present invention is employed. In FIG. 7, similar elements are numbered with the same reference numerals with respect to FIG. 5.

In the endoscope system, in which the third embodiment of the fluorescence imaging apparatus in accordance with the present invention is employed, white illumination light is passed through a rotating filter comprising blue, red, and green filter elements and is thereby separated into three-color sequential light. The sequential light is irradiated to a measuring site, and reflected light of the sequential light is detected by a CCD image sensor, which is located at a leading end of an endoscope. In this manner, three-color sequential signals are acquired. Color image signals are composed by a signal processing circuit and from the acquired three-color sequential signals. The color images signals are utilized for displaying a color image of an ordinary image on a monitor. Also, excitation light is irradiated to the measuring site, the excitation light causing the measuring site to produce fluorescence. The fluorescence produced from the measuring site is two-dimensionally acquired as a fluorescence image and with an image fiber. The fluorescence image is detected by a CCD image sensor combined with a mosaic filter constituted of an array of band-pass filter elements for transmitting only fluorescence components of the fluorescence, which fluorescence components have wavelengths falling within predetermined wavelength regions. The detected fluorescence image is displayed as a pseudo color image on a monitor. An imaging operation for detecting the fluorescence image and an imaging operation for detecting the ordinary image are performed in a time division mode. Also, an operation for sweeping out unnecessary electric charges toward a substrate direction is performed in each of the CCD image sensors.

The endoscope system, in which the third embodiment of the fluorescence imaging apparatus in accordance with the present invention is employed, comprises an endoscope 300 to be inserted into a region of a patient, which region is considered as being a diseased part, and an illuminating unit 310 provided with light sources for producing white light, which is to be separated into the three-color sequential light, and the excitation light. The endoscope system also comprises the fluorescence imaging unit 210 for receiving the fluorescence, which is produced from the measuring site in the living body when the measuring site is exposed to the excitation light, and detecting the image of the fluorescence. The endoscope system further comprises the fluorescence image processing unit 130 for performing image processing for displaying the fluorescence image as a pseudo color image in accordance with the ratio between signal intensities of fluorescence components of the fluorescence, which fluorescence components have wavelengths falling within predetermined wavelength regions. The endoscope system still further comprises an ordinary image processing unit 320 for performing image processing for displaying an ordinary image as a color image. The endoscope system also comprises the display image processing unit 150 for superimposing the color image of the ordinary image and the pseudo color image of the fluorescence image one upon the other. The endoscope system further comprises a controller 330, which is connected to the respective units and controls operation timings. The endoscope system still further comprises the monitor 170 for displaying the ordinary image (specifically, the color image of the ordinary image) and the fluorescence image (specifically, the pseudo color image of the fluorescence image), which have been superimposed one upon the other by the display image processing unit 150.

The light guide 101, the CCD cable 102, and the image fiber 103 extend in the endoscope 300 up to a leading end of the endoscope 300. A CCD image sensor 301 is connected to the leading end of the CCD cable 102. Also, the prism 109 is mounted on the CCD image sensor 301.

The CCD image sensor 301 is the interline type of CCD image sensor. In the CCD image sensor 301, signal charges, which have been formed from photoelectric conversion performed at a photosensitive section, are shifted into a transfer section and are then successively fed out from the transfer section.

The illuminating unit 310 comprises a white light source 311 for producing the white light, and an electric power source 312, which is electrically connected to the white light source 311. The illuminating unit 310 also comprises a rotating filter 313 for obtaining three-color sequential light L6 from the white light, and a filter driving section 314 for driving the rotating filter 313. The illuminating unit 310 further comprises the GaN type of semiconductor laser 114 for producing excitation light L8, which is used when the imaging operation for detecting the fluorescence image is to be performed, and the electric power source 115, which is electrically connected to the GaN type of semiconductor laser 114.

The ordinary image processing unit 320 comprises a signal processing circuit 321 for forming color image signals, which represents an ordinary image, from the three-color sequential signals, which has been obtained from the CCD image sensor 301. The ordinary image processing unit 320 also comprises the analog-to-digital converting circuit 142 for digitizing the color image signals, which have been obtained from the signal processing circuit 321. The ordinary image processing unit 320 further comprises the ordinary image memory 143 for storing the digital color image signals, which have been obtained from the analog-to-digital converting circuit 142. The ordinary image processing unit 320 still further comprises the digital-to-analog converting circuit 144 for performing digital-to-analog conversion on the color image signals, which have been received from the ordinary image memory 143. The ordinary image processing unit 320 also comprises the ordinary image encoder 145 for transforming the color image signals, which have been received from the digital-to-analog converting circuit 144, into video signals. The operations of the respective units are controlled by the controller 330. The constitution for the imaging operation for detecting the fluorescence image is the same as that in the endoscope system, in which the second embodiment described above is employed, except for the imaging timing controlled by the controller 330, which imaging timing will be described later.

How the endoscope system, in which the third embodiment of the fluorescence imaging apparatus in accordance with the present invention is employed, operates will be described hereinbelow. Firstly, how the endoscope system operates when an ordinary image is to be displayed will be described hereinbelow. Thereafter, the operation timings, with which the imaging operation for detecting the ordinary image and the imaging operation for detecting the fluorescence image are performed in the time division mode, and operations at the time of the change-over between the imaging operations will be described. The imaging operation for detecting the fluorescence image is performed in the same manner as that in the endoscope system, in which the second embodiment described above is employed, except for the imaging timing controlled by the controller 330.

When an ordinary image is to be displayed, the electric power source 312 for the white light source 311 is driven in accordance with a control signal fed from the controller 330, and the white light is produced by the white light source 311. The white light passes through the rotating filter 313, which is rotated by the filter driving section 314 under the control by the controller 330. The light having passed through the rotating filter 313 then passes through a lens 315 and impinges upon the light guide 101a as the sequential light L6 whose color changes successively to blue, green, and red. The sequential light L6 is guided through the light guide 101a to the leading end of the endoscope 300, passes through the illuminating lens 104, and is irradiated to the measuring site 10. The sequential light L6 is reflected as reflected light L7 from the measuring site 10. The reflected light L7 of the sequential light L6 is converged by the objective lens 105 and reflected by the prism 109. The reflected light L7 is then received by the photosensitive section of the CCD image sensor 301. Signal charges, which have been formed in accordance with light intensities and from photoelectric conversion performed at the photosensitive section, are shifted into the transfer section and are then successively fed into the signal processing circuit 321 of the ordinary image processing unit 320.

In the signal processing circuit 321, the processes, such as correlative double sampling, clamping, blanking, and amplification, are performed on the signals having been obtained from the CCD image sensor 301. Thereafter, with respect to each pixel, a signal intensity B3 of the blue wavelength region is detected from a blue component light image, which has been detected when the blue illumination light was irradiated as the sequential light L6 to the measuring site 10. Also, in the same manner, a signal intensity G3 of the green wavelength region and a signal intensity R3 of the red wavelength region are detected. From the thus detected signal intensities, a luminance signal Y3 and color difference signals R3–Y3 and B3–Y3, which are color image signals, are calculated.

The operation in the analog-to-digital converting circuit 142 and the subsequent operations are performed in the same manner as that in the first embodiment described above.

The operation timings, with which the imaging operation for detecting the ordinary image and the imaging operation for detecting the fluorescence image are performed in the time division mode, and operations at the time of the change-over between the imaging operations will be described hereinbelow.

Figure 8:
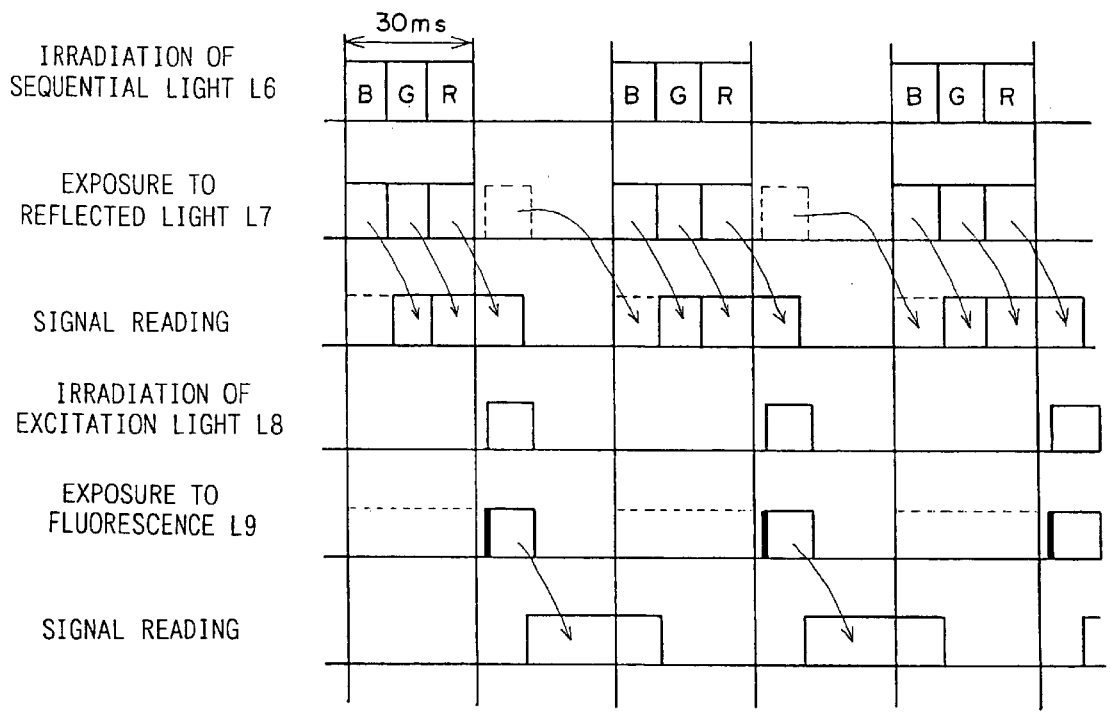
FIG. 8 is a timing chart employed in the endoscope system, in which the third embodiment of the fluorescence imaging apparatus in accordance with the present invention is employed.
Figure 9:
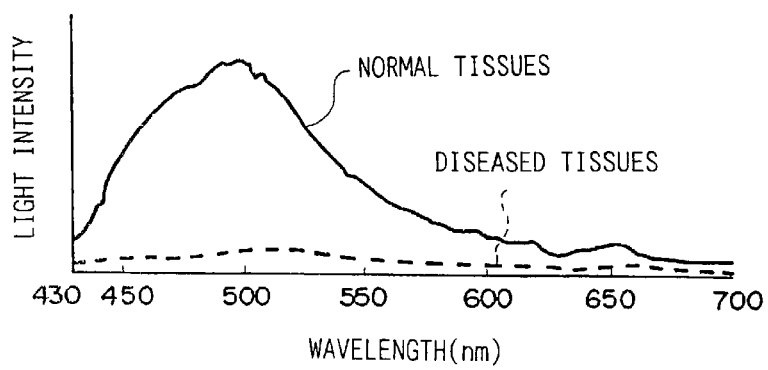
FIG. 9 is a graph showing spectral intensity distributions of fluorescence produced from normal tissues and fluorescence produced from diseased tissues.
Figure 10:
FIG. 10 is a timing chart showing timings, with which imaging operations are performed in conventional fluorescence imaging apparatuses.
Figure 10:
Figure 10:
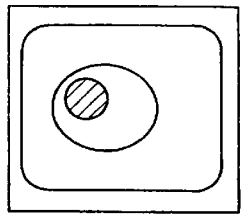
Figure 10:
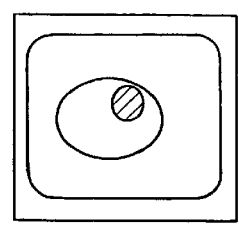

The imaging operation for detecting the fluorescence image and the imaging operation for detecting the ordinary image are performed in accordance with a timing chart illustrated in FIG. 8. As illustrated in FIG. 8, the irradiation of the sequential light L6, whose color changes successively to blue, green, and red, and the exposure of the CCD image sensor 301 to the reflected light L7 of the sequential light L6 are performed synchronously every 60 ms for a period slightly shorter than 30 ms. Each of the blue light, the green light, and the red light, which act as the sequential light L6, is irradiated for a period slightly shorter than 10 ms. Also, the detection of the blue component light image, the detection of the green component light image, and the detection of the red component light image are performed by the CCD image sensor 301 synchronously with the irradiation of the blue light, the green light, and the red light.

Specifically, when the blue light is irradiated and the irradiation of the blue light is completed after the period slightly shorter than 10 ms, the signal charges, which have been accumulated at the photosensitive section of the CCD image sensor 301 during the exposure period, are shifted into the transfer section. Thereafter, the green light is irradiated, and the blue component signal charges, which have been shifted into the transfer section, are fed out into the signal processing circuit 321. When the period slightly shorter than 10 ms has elapsed and the irradiation of the green light is completed, the signal charges, which have been accumulated at the photosensitive section of the CCD image sensor 301 during the exposure period, are shifted into the transfer section. Thereafter, the red light is irradiated, and the green component signal charges, which have been shifted into the transfer section, are fed out into the signal processing circuit 321. Further, when the irradiation of the red light is completed, the signal charges, which have been accumulated at the photosensitive section of the CCD image sensor 301 during the exposure period, are shifted into the transfer section. With the next timing, the red component signal charges are fed out from the transfer section into the signal processing circuit 321.

Also, the imaging operation for detecting the fluorescence image is performed during the period, in which the irradiation of the sequential light L6 is ceased. The irradiation of the excitation light L8 and the exposure of the CCD image sensor 211 to fluorescence L9 are performed synchronously every 60 ms for a period slightly shorter than 10 ms. When the period slightly shorter than 10 ms has elapsed and the irradiation of the excitation light L8 is completed, the signal charges, which have been accumulated at the photosensitive section of the CCD image sensor 211 during the exposure period, are shifted into the transfer section. With the next timing, the signal charges are fed out from the transfer section into the signal processing circuit 131 of the fluorescence image processing unit 130.

Therefore, as indicated by the broken line in a fifth row in FIG. 8, at the time of the imaging operation for detecting the ordinary image, the reflected light L7 of the sequential light L6 impinges upon the photosensitive section of the CCD image sensor 211 for detecting the fluorescence image and is subjected to photoelectric conversion. As a result, unnecessary signal charges are accumulated at the photosensitive section of the CCD image sensor 211. Immediately before the irradiation of the excitation light L8 is begun, the controller 330 applies a sweeping-out pulse to the CCD image sensor 211.

In the CCD image sensor 211, when the sweeping-out pulse is applied, the unnecessary signal charges are drained toward the substrate direction and are erased. Therefore, when the irradiation of the excitation light L8 is begun, the unnecessary signal charges having been accumulated at the photosensitive section of the CCD image sensor 211 have been erased. Accordingly, no problems occur with the receiving of the fluorescence L9.

As described above, the unnecessary signal charges, which have been accumulated in the CCD image sensor 211 for the detection of the fluorescence image due to the reflected light L7 of the sequential light L6 impinging upon the CCD image sensor 211 at the time of the imaging operation for detecting the ordinary image, are drained toward the substrate direction and thrown off prior to the imaging operation for detecting the fluorescence image. Therefore, adverse effects do not occur on the imaging operation for detecting the fluorescence image, and a sharp fluorescence image is capable of being detected.

Also, as indicated by the broken line in a second row in FIG. 8, at the time of the imaging operation for detecting the fluorescence image, the fluorescence L9 and reflected light L10 of the excitation light L8 impinge upon the photosensitive section of the CCD image sensor 301 for detecting the ordinary image and are subjected to photoelectric conversion. As a result, unnecessary signal charges are accumulated at the photosensitive section of the CCD image sensor 301. As in the cases of the ordinary signal charges, before the irradiation of the sequential light L6 is begun, the unnecessary signal charges are successively shifted into the transfer section. The unnecessary signal charges are then fed out from the transfer section into the signal processing circuit 321 of the ordinary image processing unit 320. In the signal processing circuit 321, the unnecessary signal charges grounded and erased.

With the operations described above, before the irradiation of the sequential light L6 is begun, the unnecessary signal charges having been accumulated in the photosensitive section of the CCD image sensor 301 have been shifted into the transfer section. Therefore, adverse effects do not occur on the receiving of the reflected light L7 of the sequential light L6. Also, before the normal signal charges having been accumulated due to the reflected light L7 of the sequential light L6 are shifted into the transfer section, the unnecessary signal charges having been shifted into the transfer section have been fed out into the signal processing circuit 321 of the ordinary image processing unit 320. Therefore, no problems occur with the shifting operation.

As described above, the unnecessary signal charges, which have been accumulated in the CCD image sensor 301 for the detection of the ordinary image due to the reflected light L10 of the excitation light L8 impinging upon the CCD image sensor 301 at the time of the imaging operation for detecting the fluorescence image, are thrown off with the operation for sweeping out unnecessary electric charges toward the substrate direction before the imaging operation for detecting the ordinary image is performed. Therefore, adverse effects do not occur on the imaging operation for detecting the ordinary image, and a sharp ordinary image is capable of being detected.

In the endoscope systems described above, in which the embodiments of the fluorescence imaging apparatus in accordance with the present invention are employed, in both the CCD image sensor for detecting the fluorescence image and the CCD image sensor for detecting the ordinary image, the operation for throwing off the unnecessary signal charges is performed. Alternatively, the embodiments described above may be modified such that, instead of the operation for throwing off the unnecessary signal charges being performed in the CCD image sensor for detecting the ordinary image, an excitation light cut-off filter, which transmits only light having wavelengths falling within a wavelength region other than the wavelength region of the excitation light, is located at the front surface of the CCD image sensor for detecting the ordinary image, and the ordinary image is detected by the color CCD image sensor via the excitation light cut-off filter. In such cases, with the simple constitution, the reflected light of the excitation light is capable of being prevented from entering into the ordinary imaging means when the imaging operation for detecting the fluorescence image is performed. Also, a sharp ordinary image is capable of being detected. In cases where the excitation light cut-off filter is thus utilized, the fluorescence, which has been produced from the measuring site during the imaging operation for detecting the fluorescence image, is not removed by the excitation light cut-off filter and impinges upon the photosensitive section of the CCD image sensor for detecting the ordinary image. However, the light intensity of the fluorescence is markedly lower than the light intensity of the ordinary image. Therefore, little effect occurs upon the imaging operation for detecting the ordinary image.

In addition, all of the contents of Japanese Patent Application No. 2000-007304 are incorporated into this specification by reference.

What is claimed is:

1. A fluorescence imaging apparatus, comprising:
   i) excitation light irradiating means for irradiating excitation light to a measuring site, the excitation light causing the measuring site to produce fluorescence,
   ii) fluorescence imaging means for performing an imaging operation for detecting a fluorescence image formed with the fluorescence, which has been produced from the measuring site when the excitation light is irradiated to the measuring site,
   iii) illumination means for irradiating illumination light to the measuring site,
   iv) ordinary imaging means for performing an imaging operation for detecting an ordinary image formed with reflected light of the illumination light, which reflected light has been reflected by the measuring site when the illumination light is irradiated to the measuring site, and
   v) control means for controlling operations of the excitation light irradiating means, the fluorescence imaging means, the illumination means, and the ordinary imaging means, such that the imaging operation for detecting the fluorescence image and the imaging operation for detecting the ordinary image are performed alternately,
      wherein the ordinary imaging means is provided with excitation light removing means for removing the excitation light from light impinging upon the ordinary imaging means.

2. An apparatus as defined in claim 1 wherein the excitation light removing means is an excitation light cut-off filter for transmitting only light having wavelengths falling within a wavelength region other than the wavelength region of the excitation light.

3. The apparatus of claim 1, wherein the excitation light comprises a blue light, and the illumination light comprises white light, wherein the blue light and the white light are emitted from respective light sources.

4. The apparatus of claim 3, wherein at least one of the ordinary imaging means and the fluorescence imaging means includes a matrix of alternating first and second bandpass filters.

5. The apparatus of claim 4, wherein the first bandpass filter has a pass band between approximately 430 and 540 nm, and the second bandpass filter has a pass band between approximately 430 and 700 nm.

6. A fluorescence imaging apparatus, comprising:
   i) excitation light irradiating means for irradiating excitation light to a measuring site, the excitation light causing the measuring site to produce fluorescence, ii) fluorescence imaging means for performing an imaging operation for detecting a fluorescence image formed with the fluorescence, which has been produced from the measuring site when the excitation light is irradiated to the measuring site, iii) illumination means for irradiating illumination light to the measuring site, iv) ordinary imaging means for performing an imaging operation for detecting an ordinary image formed with reflected light of the illumination light, which reflected light has been reflected by the measuring site when the illumination light is irradiated to the measuring site, and v) control means for controlling operations of the excitation light irradiating means, the fluorescence imaging means, the illumination means, and the ordinary imaging means, such that the imaging operation for detecting the fluorescence image and the imaging operation for detecting the ordinary image are performed alternately, wherein the ordinary imaging means is provided with excitation light removing means for removing the excitation light from light impinging upon the ordinary imaging means, and the control means controls such that an operation for flushing accumulated undesired electric charges is performed before the imaging operation of the fluorescence imaging means is performed.

7. An apparatus as defined in claim 6 wherein the excitation light removing means is an excitation light cut-off filter for transmitting only light having wavelengths falling within a wavelength region other than the wavelength region of the excitation light.

8. An apparatus as defined in claim 6 or 7 wherein the operation for flushing the accumulated charges is a dummy reading operation.

9. A fluorescence imaging apparatus, comprising:

i) excitation light irradiating means for irradiating excitation light to a measuring site, the excitation light causing the measuring site to produce fluorescence, ii) fluorescence imaging means for performing an imaging operation for detecting a fluorescence image formed with the fluorescence, which has been produced from the measuring site when the excitation light is irradiated to the measuring site, iii) illumination means for irradiating illumination light to the measuring site, iv) ordinary imaging means for performing an imaging operation for detecting an ordinary image formed with reflected light of the illumination light, which reflected light has been reflected by the measuring site when the illumination light is irradiated to the measuring site, and v) control means for controlling operations of the excitation light irradiating means, the fluorescence imaging means, the illumination means, and the ordinary imaging means, such that the imaging operation for detecting the fluorescence image and the imaging operation for detecting the ordinary image are performed alternately, wherein the control means controls such that an operation for flushing accumulated undesired electric charges is performed before at least one of: the imaging operation of the fluorescence imaging means is performed and before the imaging operation of the ordinary imaging means is performed, wherein the ordinary imaging means is provided with excitation light removing means for removing the excitation light from light impinging upon the ordinary imaging means, and wherein at least one of: the fluorescence imaging means and the ordinary imaging means comprises a substrate and an image sensor formed on the substrate, and the operation for flushing accumulated electric charges is an operation for sweeping out unnecessary electric charges towards the substrate direction during a dummy reading operation.

10. A fluorescence imaging apparatus, comprising:

i) excitation light irradiating means for irradiating excitation light to a measuring site, the excitation light causing the measuring site to produce fluorescence, ii) fluorescence imaging means for performing an imaging operation for detecting a fluorescence image formed with the fluorescence, which has been produced from the measuring site when the excitation light is irradiated to the measuring site, iii) illumination means for irradiating illumination light to the measuring site, iv) ordinary imaging means for performing an imaging operation for detecting an ordinary image formed with reflected light of the illumination light, which reflected light has been reflected by the measuring site when the illumination light is irradiated to the measuring site, and v) control means for controlling operations of the excitation light irradiating means, the fluorescence imaging means, the illumination means, and the ordinary imaging means, such that the imaging operation for detecting the fluorescence image and the imaging operation for detecting the ordinary image are performed alternately, wherein the control means controls such that an operation for flushing accumulated undesired electric charges is performed before at least one of: the imaging operation of the fluorescence imaging means is performed and before the imaging operation of the ordinary imaging means is performed, wherein at least one of the ordinary imaging means and the fluorescence imaging means includes a matrix of alternating first and second bandpass filters.

11. The apparatus of claim 10, wherein the first bandpass filter has a pass band between approximately 430 and 540 nm, and the second bandpass filter has a pass band between approximately 430 and 700 nm.

12. A fluorescence imaging apparatus, comprising:

i) excitation light irradiating means for irradiating excitation light to a measuring site, the excitation light causing the measuring site to produce fluorescence, ii) fluorescence imaging means for performing an imaging operation for detecting a fluorescence image formed with the fluorescence, which has been produced from the measuring site when the excitation light is irradiated to the measuring site, iii) illumination means for irradiating illumination light to the measuring site, iv) ordinary imaging means for performing an imaging operation for detecting an ordinary image formed with reflected light of the illumination light, which reflected light has been reflected by the measuring site when the illumination light is irradiated to the measuring site, and v) control means for controlling operations of the excitation light irradiating means, the fluorescence imaging means, the illumination means, and the ordinary imaging means, such that the imaging operation for detecting the fluorescence image and the imaging operation for detecting the ordinary image are performed alternately, wherein the control means controls such that an operation for flushing accumulated undesired electric charges is performed before at least one of: the imaging operation of the fluorescence imaging means is performed and before the imaging operation of the ordinary imaging means is performed wherein the flushing of accumulated charges for the fluorescence image is performed during irradiation of the illumination means, and the flushing of accumulated charges for the ordinary image is performed during irradiation of the excitation light irradiating means.

13. A fluorescence imaging apparatus, comprising:

i) excitation light irradiating means for irradiating excitation light to a measuring site, the excitation light causing the measuring site to produce fluorescence, ii) fluorescence imaging means for performing an imaging operation for detecting a fluorescence image formed with the fluorescence, which has been produced from the measuring site when the excitation light is irradiated to the measuring site, iii) illumination means for irradiating illumination light to the measuring site, iv) ordinary imaging means for performing an imaging operation for detecting an ordinary image formed with reflected light of the illumination light, which reflected light has been reflected by the measuring site when the illumination light is irradiated to the measuring site, and v) control means for controlling operations of the excitation light irradiating means, the fluorescence imaging means, the illumination means, and the ordinary imaging means, such that the imaging operation for detecting the fluorescence image and the imaging operation for detecting the ordinary image are performed alternately, wherein the control means controls such that an operation for flushing accumulated undesired electric charges is performed before at least one of: the imaging operation of the fluorescence imaging means is performed and before the imaging operation of the ordinary imaging means is performed, wherein the flushing of accumulated charges for the fluorescent image is performed during irradiation of one of said sequence of red, green and blue light, and the flushing of accumulated charges for the ordinary image is performed during irradiation of the blue light.

* * * * *